United States Patent [19]

Kroll et al.

[11] Patent Number: 5,549,643

[45] Date of Patent: Aug. 27, 1996

[54] OPTIMAL PULSE DEFIBRILLATOR

[75] Inventors: Mark W. Kroll; Charles U. Smith, both of Minnetonka, Minn.

[73] Assignee: Angeion Corporation, Plymouth, Minn.

[21] Appl. No.: 322,189

[22] Filed: Oct. 12, 1994

Related U.S. Application Data

[63] Continuation of Ser. No. 835,836, Feb. 18, 1992.

[51] Int. Cl.⁶ ........................................................ A61N 1/39
[52] U.S. Cl. ........................................................ 607/7
[58] Field of Search .................................... 607/5, 6, 7, 8

[56] References Cited

U.S. PATENT DOCUMENTS

| | | | |
|---|---|---|---|
| 4,821,723 | 4/1989 | Baker, Jr. et al. | 607/5 |
| 4,850,357 | 7/1989 | Bach, Jr. | 607/7 |
| 5,372,606 | 12/1994 | Lang et al. | 607/6 |

OTHER PUBLICATIONS

J. L. Prevost & F. Batelli, "Sur Quelques Effets des Deschanges * Electriques sur le Couer des Mamnifers", Comptes Mendus.
Hebdomadaires des Seances de L'Acadmie des Sciences, vol. 129, p. 1267, 1899.
Al Guyton & J Satterfield, "Factors Concerned in Defila of the Heart * Particulary Throught the Unopened Chest, Am. J. of Phys., " vol. 167, p. 81, 1951.
J.C. Schuder et al., "Transthoracic Ventricular Defib. with * Triangular and Trapezoidal Waveforms" Circ. Res., vol. 19, p. 689, Oct. 1966.
WA. Tacker, et al., "Optimum Current Duration for Capacitor-* Discharge Defib. of Canine Ventricles", J. Applied Physiology, vol. 27., p. 480, Oct. 1969.
P. S. Chen, et al., "The Potential Gradient Field Created by * Epicurdial Defib. Electrodes in Dogs", Cir. vol. 74, p. 626, Sep. 1986.
J. C. Schuder, et al., "Transthoracic Vent: Defib. in the Dog with Truncated * and Untruncated Exponential Stimuli", IEEE Trans. Biom., Nov. 1971.
M. Mirowski, et al., "Standby Automatic Defib.", Arch Int. Med., vol. * 126, p. 158, Jul. 1970.
J. C. Schuder et al., "Vent. Defib. in the Dog with a Bielectrode * Intravascular Catheter", Arch Int. Med. vol. 132. p. 286. Aug. 1973.
M. Mirowski, et al. "Cir. vol. 47, p. 79, Jan. 1973".
G. Weiss "Sur la Possibilite de Rendre Comparable? Entre Eux les * Appareils Suivant a L'Excuitation Electrique", Arch. Ital. de Biol. vol. 35, p. 413, 1901.
L. Lipicque, "Definition Experimentelle de L'Excitabilite," Proc. Soc. de Biol., vol. 77, p. 280, 1990.
J. D. Bourland et al., "Strength-Duration Curves for Trapezoidal * Waveform & Various Tilts for Transchest Defib. in Animals", Med. Instr., vol. 12, p. 38, 1978.
J. D. Bourland et al., "Comparative Efficacy of Damped * Sine Waves and Square Wave Current for Transchest Defib. in Animals", Med. Instr., vol. 12, p. 42, 1978.

*Primary Examiner*—George Manuel
*Assistant Examiner*—Scott M. Getzow
*Attorney, Agent, or Firm*—Patterson & Keough, P.A.

[57] ABSTRACT

The model that is developed in the invention is based upon the pioneering neurophysiological models of Lapicque and Weiss. The present model determines mathematically the optimum pulse duration, $d_p$, for a truncated capacitor-discharge waveform employed for defibrillation. The model comprehends the system time constant, RC, where R is tissue resistance and C is the value of the capacitor being discharged, and also the chronaxie time, $d_c$, defined by Lapicque, which is a characteristic time associated with the heart. The present model and analysis find the optimum pulse duration to be $d_p=(0.58)(RC+d_c)$. Taking the best estimate of the chronaxie value from the literature to be 2.7 ms, permits one to rewrite the optimum pulse duration as $d_p=(0.58)RC+1.6$ ms. The apparatus makes use of the mathematical definition of optimum pulse duration by storing in the control circuitry of the defibrillation system the actual measured value of the particular capacitor incorporated in the system. The optimized-pulse prescription of this invention can be applied to a monophasic waveform, or to either or both of the phases of a biphasic waveform.

23 Claims, 6 Drawing Sheets

Fig. 4

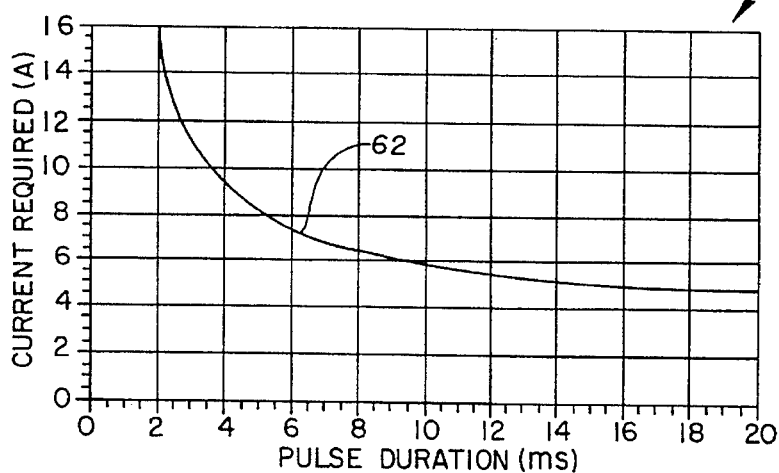

Fig. 5

| | AUTHOR | YEAR | ANIMAL (ELECTRODES) | DC SOURCE | DC |
|---|---|---|---|---|---|
| 1. | GOLD | 1977 | CALF (CHEST) | DETERMINED | 2.7ms |
| 2. | BOURLAND | 1978 | PONY (CHEST) | DETERMINED | 3.6 |
| 3. | WESSALE | 1980 | DOG (ENDOCARDIAL CATHETER) | GIVEN | 1.8 |
| 4. | JONES | 1982 | CULTURED CHICK CELLS IN DIASTOLE | GIVEN | 1.8 |
| 5. | NIEBAUER | 1983 | DOG (ISOLATED HEART IN FLUID BATH) | DETERMINED | 4.1 |
| 6. | GEDDES | 1985 | DOG (ISOLATED HEART IN FLUID BATH) | AVERAGED | 2.8 |
| 7. | FEESER | 1990 | DOG (EPICARDIAL PATCHES) | DETERMINED | 2.0 |

1. J.H. GOLD, et al., *CIRCULATION*, VOL. 56, p.745, NOVEMBER 1977.

2. J.D. BOURLAND, et al., *MED. INSTR.*, VOL. 12, p. 38, 1978.

3. J.L. WESSALE, et al., *J. ELECTROCARDIOLOGY*, VOL.13, p. 359, 1980.

4. J.L. JONES AND R.E. JONES, *AM I PHYSIOL.*, VOL. 242, p. H662, 1982.

5. M.J. NIEBAUER, et al., *CRIT. CARE MEDICINE*, VOL. 11, p. 95, FEBRUARY 1983.

6. L.A. GEDDES, et al., *MED. BIOL. ENG. COMP.*, VOL. 23, p. 122, 1985.

7. S.A. FEESER, et al., *CIRCULATION*, VOL. 82, p.2128, DECEMBER 1990.

Fig. 6

PHYSIOLOGICALLY EFFECTIVE CURRENT I pe ACHIEVED USING THREE DIFFERENT METHODS FOR SPECIFYING A MONOPHASIC WAVEFORM.

| RESISTANCE | 65% TILT | FIXED PULSE DURATION OF 6ms | OPTIMUM DURATION |
|---|---|---|---|
| 25 ohms | 10.70 A | 9.89 A | 10.71 A |
| 50 | 6.79 | 6.94 | 6.96 |
| 100 | 3.92 | 4.20 | 4.23 |

OPTIMAL PULSE DEFIBRILLATOR

This is a continuation of application Ser. No. 08/835,836, filed Feb. 18, 1992, pending.

BACKGROUND OF THE INVENTION

1. Field of the Invention

The present invention relates generally to defibrillation methods, and more particularly, to an optimum truncated capacitive-pulse duration that is based upon the time constants of the system and of the heart.

2. Description of the Prior Art

Defibrillation, or causing the cessation of chaotic and uncoordinated contraction of the ventricular myocardium by application of an electrical direct current and voltage, in its most primitive form, goes back to the last century. [J. L. Prevost and F. Batelli, "Sur Quelques Effets des Descharges Electrriques sur le Couer des Mammifers", *Comptes Rendus Hebdomadaires des Seances de L'Acadmie des Sciences*, Vol. 129, p. 1267, 1899.] Because of the large currents required for defibrillation, large-area electrodes are employed. [A. C. Guyton and J. Satterfield, "Factors Concerned in Defibrillation of the Heart, Particularly Through the Unopened Chest", Am. J. of Physiology, Vol. 167, p. 81, 1951.]

For reasons of simplicity and compactness, capacitor-discharge systems are almost universally used in defibrillation. The discharge of a capacitor C through a resistance R results in a curve of voltage versus time (and hence, of current versus time as well) that is a declining exponential function, with a characteristic time given by the product RC. But it has also been recognized for some time that the long-duration, low-amplitude "tail" of the capacitor-discharge pulse is detrimental [J. C. Schuder, G. A. Rahmoeller, and H. Stoeckle, "Transthoracic Ventricular Defibrillation with Triangular and Trapezoidal Waveforms", Circ. Res., Vol. 19, p. 689, October, 1966; W. A. Tacker, et al., "Optimum Current Duration for Capacitor-discharge Defibrillation of Canine Ventricles", J. Applied Physiology, Vol. 27, p. 480, October, 1969.] The exact reason for this detrimental effect is not known, although plausible speculations exist, with one possibility being that field heterogeneties cause arthythmias in significantly large regions of the heart. [P. S. Chen, et al., "The Potential Gradient Field Created by Epicardial Defibrillation Electrodes in Dogs", Circulation, Vol. 74, p. 626, September, 1986.] A convenient way to eliminate the low-amplitude "tail" of a capacitor discharge is by switching, which is to say, simply opening the capacitor-load circuit after a predetermined time, or else when voltage has fallen to a particular value. For this reason, the time-truncated capacitor discharge has been extensively used after its effectiveness was first demonstrated [J. C. Schuder, et al., "Transthoracic Ventricular Defibrillation in the Dog with Truncated and Untruncated Exponential Stimuli", IEEE Trans. Biom. Eng., Vol. BNF-18., p. 410, November 1971.]

The defibrillation effectiveness of time-truncated capacitor discharges can be convincingly shown by comparing an untruncated waveform and a truncated waveform of equal effectiveness. The full discharge waveform 10 of FIG. 1A was generated by charging a 140-NF capacitor to 455 V, for an energy delivery of 30 J. But the truncated waveform 20 shown in FIG. 1B was equally effective for defibrillation in spite of having about only half the energy, and a lower initial voltage. This demonstration was carried through for the case of dogs using a catheter electrode and a subcutaneous patch [M. Mirowski, et al., "Standby Automatic Defibrillator", Arch. Int. Med., Vol. 126, p. 158, July, 1970], as well as with a dual-electrode intraventricular catheter. [J. C. Schuder, et al., "Ventricular Defibrillation in the Dog with a Bielectrode Intravascular Catheter", Arch. Int. Med., Vol. 132, p. 286, August, 1973.] The latter electrode arrangement was also used to demonstrate the point for the case of man. [M. Mirowski, et al., "Feasibility and Effectiveness of Low-energy Catheter Defibrillation in Man", Circulation, Vol. 47, p. 79, January, 1973.] Such demonstrations that compact capacitor-storage systems could be used with effectiveness paved the way for implantable defibrillator system.

In spite of the dramatic results obtained with time-truncated capacitor-discharge defibrillator systems, the waveform specifications have not been systematically optimized. For example, some manufacturers such as Medtronic (in their PCD product) simply specify pulse duration, although the physician can choose and adjust the value. A typical value might be a programmable duration of 6 ms. Other manufacturers such as Cardiac Pacemakers (in their Ventak product) specify the relative amount of voltage decline at the time of truncation, with a typical value of the decline being 65% of the initial voltage. It has become customary to use the term "tilt" to describe the relative amount of such voltage decline, expressed either as a decimal fraction or a percentage. In algebraic language:

$$\text{tilt} = (V_{initial} - V_{final})/V_{initial} \qquad \text{Eq. 1}$$

Both of the systems just cited employ the monophasic waveform. This means that it consists of a single-polarity single pulse, specifically a time-truncated capacitor-discharge waveform like that of FIG. 1B. However, biphasic waveforms are also widely used. In this case capacitor discharge is also used, but instead of truncation, polarity reversal is accomplished (by switching once more), so that a second opposite-polarity pulse immediately follows the initial pulse, and is then itself truncated. The result is illustrated in FIG. 2.

Prior art in waveform specification for biphasic systems is parallel to that for monophasic systems. Specifically, some systems simply specify initial-pulse duration. [Baker, Intermedics, U.S. Pat. No. 4,821,723.] Other systems specify tilt. [Bach, Cardiac Pacemakers, U.S. Pat. No. 4,850,537.] The central focus of the present invention is to optimize pulse duration by using the model of this invention, which comprehends both the time constant of the system (capacitor and load resistance), and the natural time constant of the heart as explained below.

It is worthwhile to examine specific examples of prior-art waveform specification. In FIG. 3A is shown the simple pulse-duration specification, applicable to either monophasic pulses or biphasic initial pulses. And in FIG. 3B is shown a tilt specification, also applicable to either monophasic pulses or biphasic initial pulses.

The foundation for optimizing the time-truncated waveform is a family of mathematical neurophysiological models for tissue stimulation going back to the turn of the century, with the first important such model having been developed by Weiss. [G. Weiss, "Sur la Possibilite de Rendre Comparable entre Eux les Appareils Suivant a l'Excitation Electrique", Arch. Ital. deBiol., Vol. 35, p. 413, 1901.] He employed the ballistic-rheotome technique for pulse generation, wherein a rifle shot of known velocity is used to cut two wires in sequence, their spacing being set and measured. Cutting the first wire eliminated a short from a dc source, causing current to flow through the tissue under test, and cutting the second wire opened the circuit, terminating the pulse applied. Converting the electrical data into charge delivered by the pulse, Weiss found that the charge Q needed for stimulation was linearly dependent on pulse duration, $d_p$. Specifically, $$Q = K_1 + K_2 d_p \qquad \text{Eq. 2}$$

Subsequently and similarly, the physiologist L. Lapicque collected substantial amounts of data on the amount of current required for tissue stimulation, using constant-current pulses of various durations. [L. Lapicque, "Definition Experimentelle de l'excitabilite," Proc. Soc. deBiol., Vol. 77, p. 280, 1909.] Lapicque established an empirical relationship between the current I and the pulse duration $d_p$, having the form:

$$I = K_1 + (K_2/d_p) \qquad \text{Eq. 3}$$

(Note that multiplying this expression through by $d_p$ yields an expression in charge rather than current, identically the equation given by Weiss. Thus, $K_1 = k_1/d_p$ and $K_2 = k_2 d_p$.)

Equation 3 of Lapicque shows that the necessary current and the pulse duration are related by a simple hyperbola, shifted away from the origin by the amount of the constant term $K_1$. Hence the stimulating current required in a pulse of infinite duration is $K_1$, a current value Lapicque termed the rheobase. Shortening the pulse required progressively more current, and the pulse length that required a doubling of current for excitation, or $2K_1$, he termed the chronaxie, $d_c$. Substituting $2K_1$ and $d_c$ into Eq. 3 in place of I and $d_p$, respectively, yields:

$$d_c = K_2/K_1 \qquad \text{Eq. 4}$$

For the sake of specific illustration, assume a rheobase current of 3.7 amperes, and a chronaxie time of 6 milliseconds. Then a plot of current strength required versus the pulse duration that must accompany it is as shown in FIG. 4.

Lapicque's model described cell stimulation, rather than defibrillation, but Bourland demonstrated that defibrillation thresholds in dogs and ponies followed the Lapicque model, provided average current is used in the exercise. [J. D. Bourland, W. Tacker, and L. A. Geddes, "Strength-Duration Curves for Trapezoidal Waveforms of Various Tilts for Transchest Defibrillation in Animals", Med. Instr. Vol. 12, p. 38, 1978.] In a companion paper, the same workers showed that average current is a useful and consistent measure of defibrillation effectiveness for time-truncated pulses of a fixed duration through a substantial range of durations, from 2 to 20 milliseconds; in other words, so long as the exponential "tail" is eliminated, pulse effectiveness is not very dependent upon waveform details. [J. D. Bourland, W. Tacker, and L. A. Geddes, "Comparative Efficacy of Damped Sine Waves and Square Wave Current for Transchest Defibrillation in Animals", Med. Instr., Vol. 12, p. 42, 1978].

The defibrillation chronaxie for the heart is usually between 2 ms and 4 ms, as can be seen in the chart of FIG. 5. (A journal citation for each entry is given below the chart.) In this synopsis of published data, chronaxie was inferred from a strength-duration curve such as that of FIG. 4 when such a curve was provided, and these care labeled "given"; in the case labeled "determined", chronaxie was calculated from discrete data provided. In the only other case (6. Geddes, et al.), curves were given for waveforms of various tilts, and these were averaged to arrive at 2.8 ms. For the overall chart, 2.7±0.9 ms is the average chronaxie value.

SUMMARY OF THE INVENTION

The inventors have developed an analytic method for waveform optimization. It builds upon the models of Lapicque and Weiss, the finding of Bourland, and the data summarized in FIG. 5. To do this one first defines a "sufficiency ratio", the ratio of Bourland's ruling average current and the current needed for defibrillation according to the Lapicque model for a heart of a given $K_1$, rheobase current, and a given $K_2$, a charge. Algebraically, $$\text{Sufficiency ratio} = \frac{I_{ave}}{K_1 + \frac{K_2}{d_p}} \qquad \text{Eq. 5}$$

It is simply the ratio of Bourland's available therapeutic current (or the average current $I_{ave}$) to the current required according to the Lapicque formulation. Hence for a ratio of unity, the waveform of average current $I_{ave}$ and duration $d_p$ will be able to defibrillate a heart characterized by $K_1$ and $K_2$.

Multiplying Eq. 5 through by the rheobase current $K_1$ yields an expression that of course has dimensions of amperes; noting from Eq. 4 that $K_1 d_c = K_2$, makes it possible to eliminate the heart-characterizing quantities $K_1$ and $K_2$ from this expression.

$$\frac{I_{ave}}{1 + \frac{K_2}{K_1 d_p}} = \frac{I_{ave}}{1 + \frac{d_c}{d_p}} \qquad \text{Eq. 6}$$

Thus, we have here an expression in the two pulse-characterizing quantities $I_{ave}$ and $d_p$, but in only one heart-characterizing quantity, the chronaxie time. Note that for an infinite pulse duration, this current simply equals the average current $I_{ave}$, but for a pulse of finite duration, it will be smaller than $I_{ave}$. This current, therefore, measures the effectiveness of a particular waveform in defibrillating a particular heart. For this reason, the inventors have named it the Physiologically effective current, or $I_{pe}$, which can then be further manipulated in straightforward fashion.

$$I_{pe} = \frac{I_{ave} d_p}{d_c + d_p} \qquad \text{Eq. 7}$$

Note further that $I_{pe}$ would be the same as $I_{ave}$ if one had a zero value of chronaxie time, $d_c$. In this sense, Eq. 7 constitutes a correction from actual average current necessitated by the chronaxie phenomenon. Since, $$V_f = V_i e^{-dp/Rc} \qquad \text{Eq. 8}$$

it follows that delivered charge $$= C(V_i - V_f) = CV_i(1 - e^{-dp/RC}) \qquad \text{Eq. 9}$$

and hence $$I_{pe} = \frac{CV_i(1 - e^{-dp/RC})}{d_p + d_c} \qquad \text{Eq. 10}$$

It is clear that $I_{pe}$ vanishes at both extremes of $d_p$, so that intermediate extremum must be a maximum, defining explicitly the optimum waveform that can be achieved by varying pulse duration with a particular average current. To determine this optimum pulse duration, let RC=t, and set $$\frac{dI_{pe}}{dd_p} = CV_i \frac{(d_p + d_c(e^{-d/t})) - (1 - e^{-d/t})}{(d_p + d_c)^2} = 0 \qquad \text{Eq. 11}$$

Hence, using the system time constant (t=RC) for normalization yields $$Z = \frac{d_p}{t} \qquad \text{Eq. 13}$$

and $$\alpha = \frac{d_c}{t} \qquad \text{Eq. 14}$$

Using these definitions, $$(Z+\alpha+1)e^{-z}-1=0 \qquad \text{Eq. 15}$$

Next, multiply through by $-e^{-z}$ to obtain the simplified equation whose root is sought.

$$e^z - z - \alpha - 1 = 0 \qquad \text{Eq. 16}$$

Because the equation is transcendental, it cannot be solved in close form, so define the function on the left-hand side as $f(z)$ and the first approximation for its root as $z_o$. The Newton-Raphson method gives an approximate value for the root as $$Z^1 = Z_o - \frac{f(Z_o)}{f'(Z_o)} \qquad \text{Eq. 17}$$

Experience shows that waveforms with a tilt of about 65% are effective, and this corresponds to $d_p=t$, or $z_0=1$. Hence an appropriate approximate root is:

$$Z^1 = 1 - \frac{e-1-\alpha-1}{e-1} = \frac{1+\alpha}{e-1} \qquad \text{Eq. 18}$$

Denormalization yields:

$$d_p = t \frac{1+d_c/t}{e-1} = \frac{t+d_c}{e-1} \qquad \text{Eq. 19}$$

for the approximate optimum value of pulse duration $d_p$ as a function of chronaxie $d_c$ and system time constant t. Carrying through the optimization numerically shows that this estimate is valid within 0.2% for typical values of R, C, and $d_c$. Even for extreme values of these system and heart parameters, the approximate value of optimum duration produces a value for the current $I_{pe}$ that is within 2% of the optimum. Since $(e-1)=1.72\approx2$, the optimum pulse duration is approximately (and somewhat larger than) the average of the system's time constant t and the heart's characteristic time $d_c$. In other words, the optimum pulse duration is a compromise between the two characteristic times involved.

Equation 19 for optimal pulse duration can be rewritten as:

$$d_p=(0.58)(RC+d_c) \qquad \text{Eq. 20}$$

Thus, the optimum pulse duration is most naturally specified as a fraction of the sum of two characteristic times: that for the system, RC, and that for the heart, the chronaxie time $d_c$. Letting $d_c=2.7$ ms, this becomes:

$$d_p=(0.58)RC+1.6 \text{ ms} \qquad \text{Eq. 21}$$

Because the sensing of tilt is easy, using tilt as a criterion for pulse termination is straightforward and convenient. Therefore, we define for present purposes a new term, intermediate tilt, to be the ratio (usually expressed as a percentage) of the voltage at some intermediate part of the pulse to the initial voltage. Next, convert $(0.58)RC$ into intermediate tilt:

Voltage ratio$-(0.58)RC/RC$ $=1-e^{-0.58}$ $=1-0.56=0.44 \qquad \text{Eq. 22}$

Thus, intermediate tilt=44% $\qquad \text{Eq. 23}$ so that the convenient alternate method for expressing optimum pulse duration is $$d_p=\{44\% \text{ intermediate tilt}\}+1.6 \text{ ms} \qquad \text{Eq. 24}$$

where the symbols { } are taken to mean "time interval for". This new method for specifying an optimal pulse is illustrated in FIG. 3C, for comparison with the prior art method illustrated in FIGS. 3A and 3B.

It is evident that the optimum-duration criterion of the present invention could be translated into an equivalent tilt specification if the value of R were well-known, stable over time and constant from patient to patient. But typical resistance variation is from some 25 ohms to 100 ohms. Furthermore, variations in capacitance exist, with 10% tolerances being typically encountered. Because the new criterion takes account of such variations, it is clearly superior to both a fixed-tilt and a fixed-duration specification. To illustrate this superiority we calculate physiologically effective current $I_{pe}$ in the face of resistance variations. The higher the $I_{pe}$, the better the criterion. In FIG. 6 is shown the result of such calculations for the popular fixed-tilt (65%) and fixed-duration (6 ms) criteria, as compared to the optimum-duration criterion of the present invention. Note that the optimum-duration criterion yields a higher $I_{pe}$ than either of the prior-art criteria through the full resistance range.

The method of the present invention can be applied in the biphasic case to the first pulse or phase, to the second phase, or to both. If the first phase is chosen for optimum duration, there are a number of other ways to specify the second phase. For example, the second phase can be permitted to decay to an 80% overall tilt, or 80% charge removal from the capacitor. This method has the advantage of delivering fixed energy to the defibrillation path, irrespective of the kinds of variations discussed above. Another method lets the duration of the second pulse equal a fraction of that determined to be optimal for the first. Limited animal studies indicate a benefit with respect to having the second pulse less than or equal to the first in duration. Finally, the second pulse could be made to meet a fixed-tilt or fixed-duration specification, just as in the prior-art monophasic cases.

One significant aspect and feature of the present invention is a defibrillation waveform of optimum duration.

Another significant aspect and feature of the present invention is a pulse duration that comprehends the system time constant, RC, and the heart's characteristic time, the chronaxie, $d_c$.

Still another significant aspect and feature of the present invention is a pulse duration that is approximately an average of the system time constant, RC, and the heart's characteristic time, the chronaxie, $d_c$.

Still another significant aspect an feature of the present invention is a pulse duration that is equal to the sum of the time interval corresponding to an intermediate tilt of 44% and 1.6 ms.

Another significant aspect and feature of the present invention is the programming of actual values of R, C, and $d_c$ into the control circuitry of the defibrillation system.

Still another significant aspect and feature of the present invention is the use of a defibrillation pulse of optimum duration in a monophasic waveform.

Yet another significant aspect and feature of the present invention is the use of a defibrillation pulse of optimum duration in at least one phase of a biphasic waveform.

Another significant aspect and feature of the present invention is the use of a defibrillation pulse of optimum duration in one phase of a biphasic waveform, with the other phase having an equal duration.

Still another significant aspect and feature of the present invention is the use of a defibrillation pulse of optimum duration in one phase of a biphasic waveform, with the other phase having a duration fixed by overall tilt.

Yet another significant aspect and feature of the present invention is an increase of defibrillation effectiveness for a given capacitor volume and system volume.

Having thus described embodiments of the present invention, it is a principal object of the present invention to employ a defibrillation waveform of optimum duration.

A further object of the present invention is to employ a pulse duration that comprehends the system time constant, RC, and the heart's characteristic time, the chronaxie, $d_c$.

A still further object of the present invention is to employ a pulse duration that is approximately an average of the system time constant, RC, and the heart's characteristic time, the chronaxie, $d_c$.

Still another object of the present invention is to employ a pulse duration that is a function of actual measurement of the system time constant, RC.

Another object of the present invention is to use a pulse duration that is the sum of a time interval corresponding to an intermediate tilt of 44% and a fixed time interval of 1.6 ms.

A further object of the present invention is to employ a defibrillation pulse of optimum duration in at least one phase of a biphasic waveform.

Yet a further object of the present invention is to employ a defibrillation pulse of optimum duration in one phase of a biphasic waveform, with the other phase having an equal duration.

A still further object of the present invention is to employ a defibrillation pulse of optimum duration in one phase of a biphasic waveform, with the other phase having a duration fixed by overall tilt.

Yet a further object of the present invention is to achieve an increase of defibrillation effectiveness for a given capacitor volume and system volume.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 4 illustrates a chart of average current strength required for defibrillation versus the duration of the pulse of that average current;

FIG. 5 illustrates a chart of chronaxie values drawn from the literature and a listing of the reference citations; and, FIG. 6 illustrates a chart of physiologically effective current values achieved by three waveform-specifying methods in the face of load-resistance variations.

DETAILED DESCRIPTION OF THE PREFERRED EMBODIMENTS

Figure 1A:
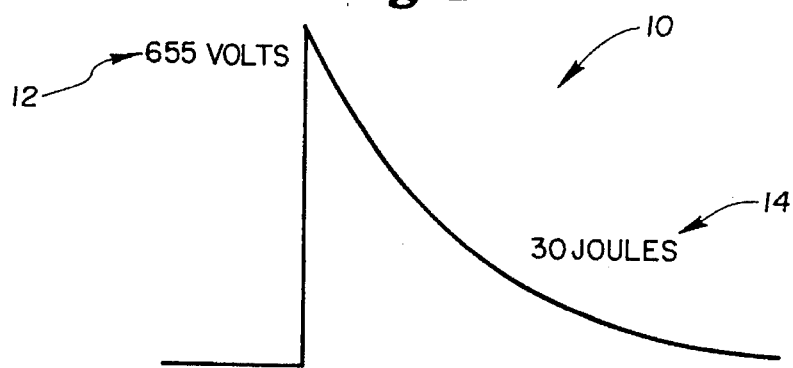
FIG. 1A illustrates a particular voltage-time waveform of a capacitor discharged through a resistor.

FIG. 1A illustrates a particular voltage-time waveform 10 of a capacitor discharged through a resistor, incorporating a particular initial voltage 12, and a particular energy 14 delivered from the capacitor to the resistor.

Figure 1B:
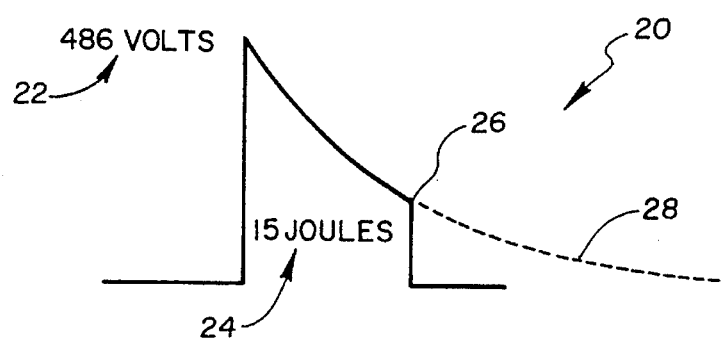
FIG. 1B illustrates a particular voltage-time waveform of a time-truncated pulse, produced by discharging a capacitor through a resistor and terminating the pulse by switching, with this pulse delivering half the energy of that in FIG. 1A.

FIG. 1B illustrates a particular voltage-time waveform 20 of a capacitor discharged through a resistor, incorporating a particular initial voltage 22, and a particular energy 24 delivered from the capacitor to the resistor, and also incorporating time-truncation of the pulse, produced by terminating the pulse through switching at the particular time 26, thus eliminating the tail 28 of the pulse, with this particular pulse delivering half the energy of the particular pulse in FIG. 1A.

Figure 2:
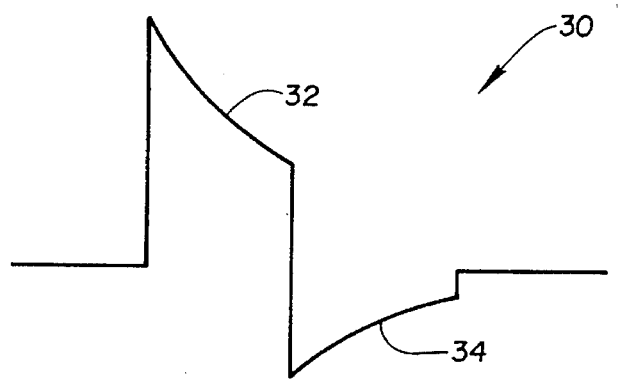
FIG. 2 illustrates a biphasic waveform for defibrillation.

FIG. 2 illustrates a biphasic voltage-time waveform 30 for defibrillation, incorporating a first phase 32 and a second phase 34 of opposite polarity.

Figure 3A:
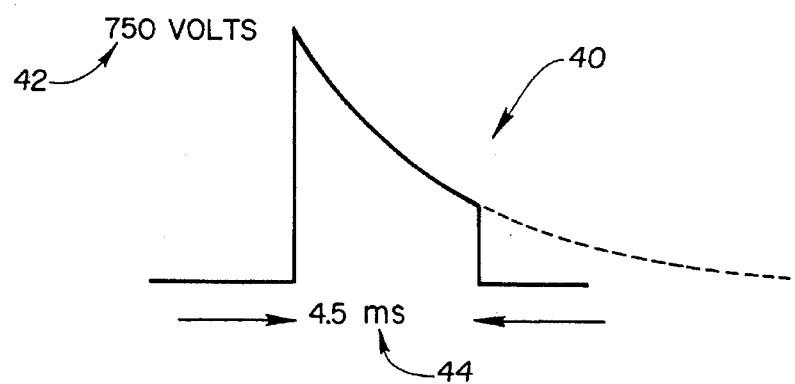
FIG. 3A illustrates a monophasic waveform of a particular initial voltage, specified in terms of pulse duration.

FIG. 3A illustrates a monophasic voltage-time waveform 40 of a particular initial voltage 42 specified in terms of a specific pulse duration 44 of 4.5 ms.

Figure 3B:
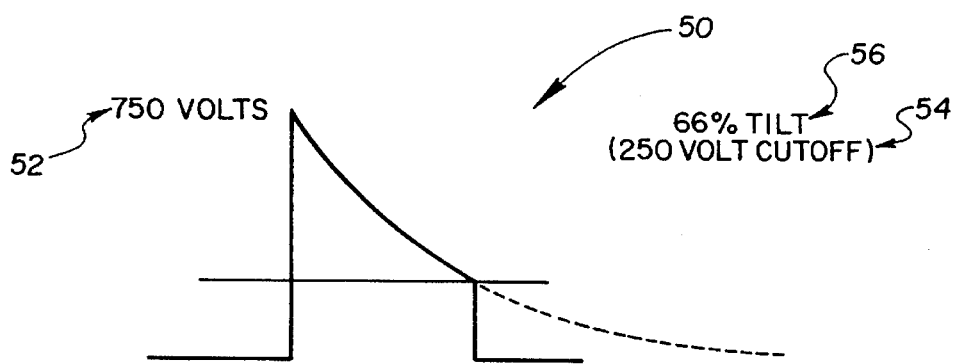
FIG. 3B illustrates a monophasic waveform of a particular initial voltage, specified in terms of tilt.

FIG. 3B illustrates a monophasic voltage-time waveform 50 of a particular initial voltage 52, with the waveform specified in terms of a final voltage 54, with the ratio of the voltage decline at truncation to the initial voltage 52 commonly being described as a tilt percentage 56.

Figure 3C:
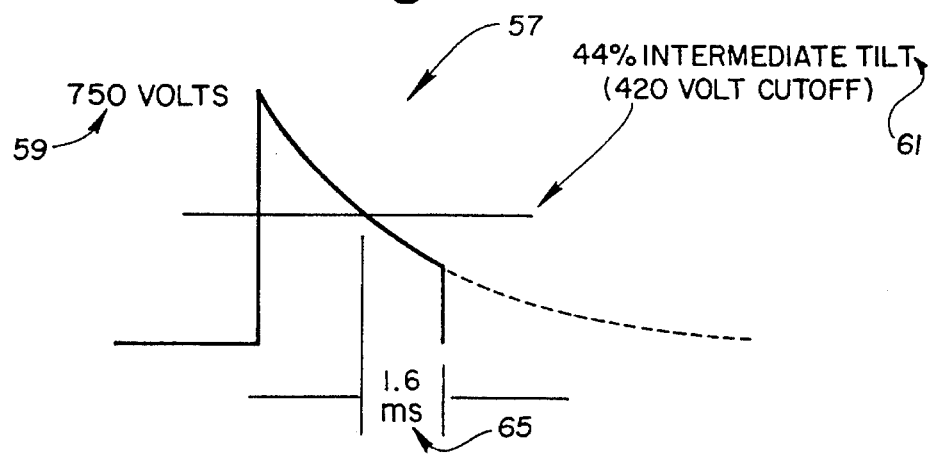
FIG. 3C illustrates a monophasic waveform of a particular initial voltage specified by the method of the present invention.

FIG. 3C illustrates a monophasic voltage-time waveform 57 of a particular initial voltage 59 with the waveform specified in terms of a time interval corresponding to an intermediate tilt 61 of 44%, plus a fixed time interval 65 of 1.6 ms.

FIG. 4 illustrates a chart 60 that incorporates a curve 62 of average current strength required for defibrillation versus the duration of the pulse of that average current.

FIG. 5 illustrates a chart 70 of chronaxie values 72, these data taken out of the literature and drawn from the list 74 of cited references.

FIG. 6 illustrates a chart 80 of physiologically effective current values achieved by two defibrillation waveform-specifying methods 82 and 84 of the prior art, and from the waveform-specifying method 86 of the present invention, all in the face of variations in load-resistance values 88, illustrating the superiority of the method 86 of the present invention.

MODE OF OPERATION

The present invention makes use of the mathematical definition of optimum pulse duration by storing in the control circuitry of the defibrillation system the actual value of the particular capacitor incorporated in the system.

It will be recognized that the control circuitry of the defibrillation system can be implemented in a variety of ways, as described, for example, in U.S. Pat. Nos. 4,821,723 and 4,850,357, and is preferably implemented so as to include a microprocessor with associated memory as described in detail, for example, at Cols. 9 and 10 of U.S. Pat. No. 4,821,723, or as specific electronic control circuitry as described in detail, for example, at Col. 2 of U.S. Pat. No. 4,850,357.

The optimized-pulse prescription of this invention can be applied to a monophasic waveform, or to either or both of the phases of a biphasic waveform. In the latter case, when it is applied to a single phase, the other can be specified to have equal duration. Another option specifies the opposite phase in a way that produces a particular overall tilt, or degree of discharging of the capacitor.

Figure 7:
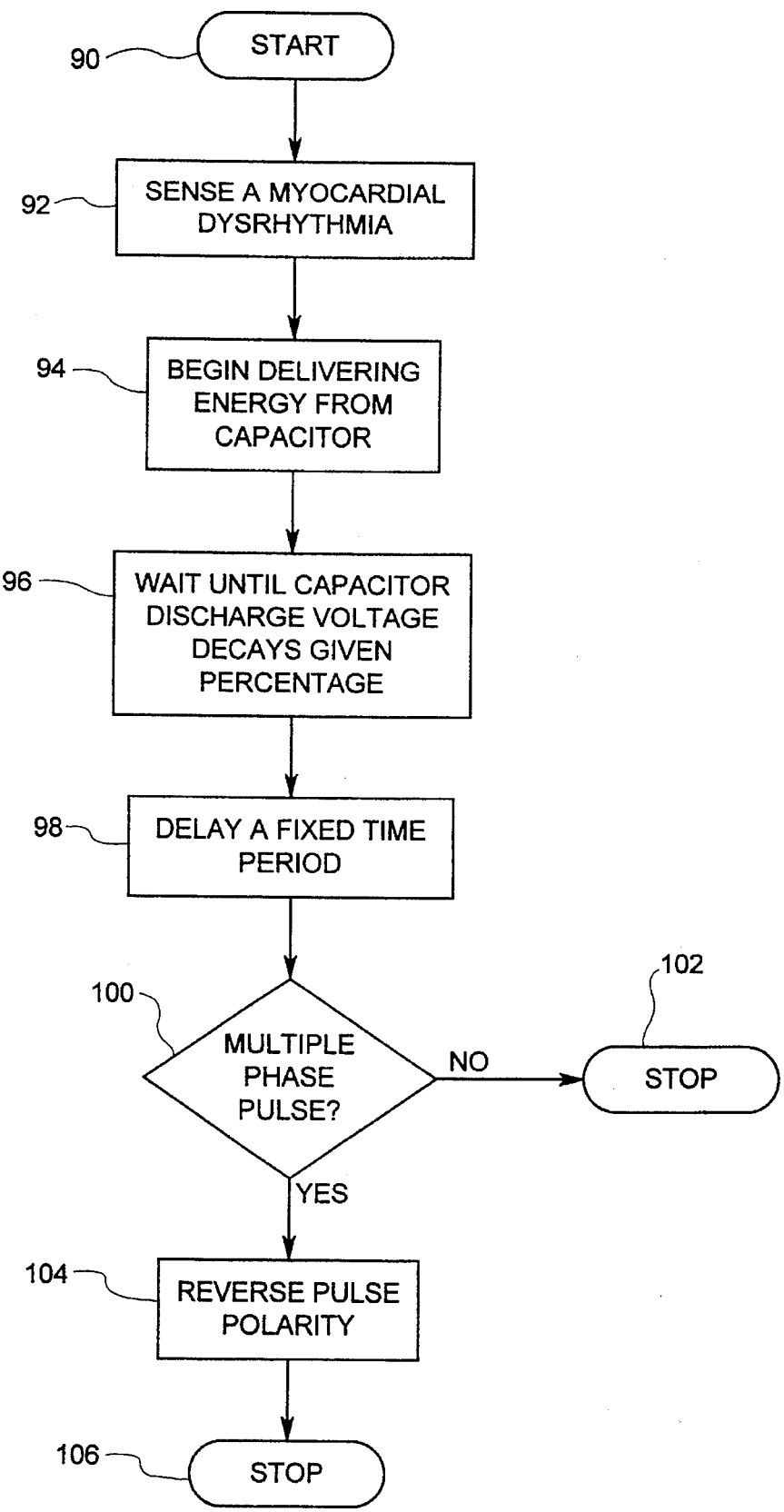
FIG. 7 is a flow chart showing the decisional steps of a preferred embodiment of the present invention.

Referring now to FIG. 7, the decisional steps of a preferred embodiment of the present invention will now be described. The method of operating a defibrillator begins by sensing a myocardial dysrhythmia in a human patient (steps 90, 92). After the myocardial dysrhythmia is sensed, capacitor energy begins to be delivered to the heart (step 94). Capacitor energy continues to be discharged until the capacitor discharge voltage decays a given percentage from the preselected amount of electrical energy stored in the capacitor (step 96). For example, with a decay of 44%, the time period is 0.58 of the RC time constant as indicated by $44\% = 1 - e^{-0.58}$ (Equations 22–24). Energy delivery continues for another fixed time period after reaching the desired voltage decay percentage (step 98). For example, a fixed time period value of 1.6 ms is equal to 0.58 of the heart's assumed chronaxie duration of 2.7 ms (Equations 20, 21).

Next, if a monophasic pulse is sufficient, the delivery of energy from the capacitor is halted (steps 100, 102). If a biphasic or multiple phase pulse is required, then voltage polarity is reversed as energy is discharged (steps 100, 104) until the discharge is complete (step 106).

Figure 8:
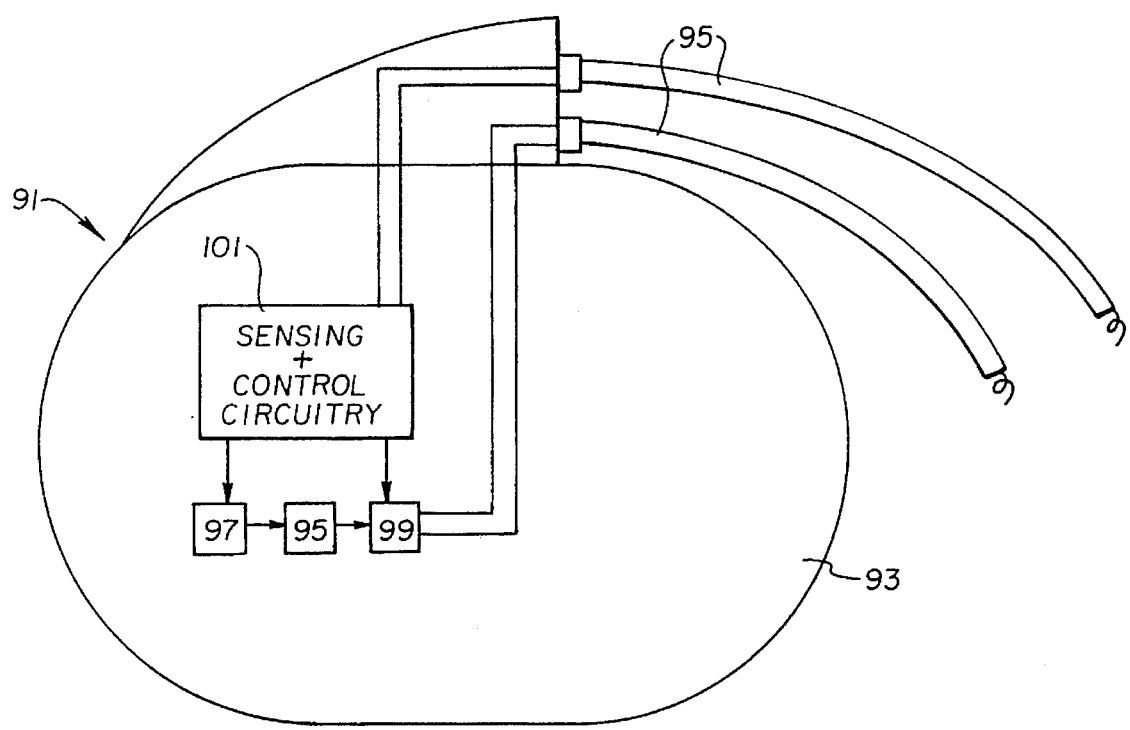
FIG. 8 illustrates a schematic representation of an implantable cardioverter defibrillator.

Referring now to FIG. 8, a schematic illustration of an implantable cardioverter defibrillator (ICD) 91 will now be described. ICD 91 is illustrated having a housing 93 and a pair of electrodes 95. The electrodes are adapted for implantation in a human patient as is housing 93. Housing 93 contains a wave form generating capacitor means 95 for storing an electrical charge and a capacitor charging means 97 for charging capacitor means 95. An output switch 99 is provided to selectively discharge the electrical charge in capacitive means 95. A sensing and control circuit 101 is provided to sense cardiac dysrhythmia from a human patient and to provide a control signal to switch means 99.

Various modifications can be made to the present invention without departing from the apparent scope hereof.

We claim:

1. An improved implantable defibrillator apparatus for producing a capacitive-discharge defibrillation waveform to be delivered through at least two electrodes adapted for implantation in a human patient, the implantable defibrillator apparatus including a self-contained human implantable housing having electrical connections to at least two electrodes adapted for implantation in the human patient, the implantable housing containing a waveform-generating capacitor means for storing an electrical charge, means for charging the waveform-generating capacitor means, and means for selectively discharging the electrical charge in the capacitor means through the at least two electrodes in response to a control signal from a means for sensing of a cardiac dysrhythmia in the human patient, the improvement comprising:

the means for selectively discharging including means for controlling the discharge of the capacitor means through the at least two electrodes to produce a defibrillation waveform comprising at least one electrical pulse having a predetermined optimum pulse duration based on an optimization of an effective current of the defibrillation waveform for a preselected amount of electrical energy stored in the capacitor means.

2. The apparatus of claim 1 wherein the optimum pulse duration is automatically set by the apparatus to be the sum of:

a first value derived from a fixed time period; and a second value derived from the time required for a truncated discharge of the capacitor means as controlled by the means for selectively discharging to decay by a particular percentage of the preselected amount of electrical energy stored in the capacitor means.

3. The apparatus of claim 2 wherein the first value is between 1.5 ms and 1.7 ms.

4. The apparatus of claim 2 wherein the first value is 1.6 ms.

5. The apparatus of claim 2 wherein the percentage decay is between 40% and 48%.

6. The apparatus of claim 2 wherein the percentage decay is 44%.

7. The apparatus of claim 1 wherein the optimum pulse duration is automatically set by the apparatus to be approximately the average of:

a first time constant that is a system time constant, RC, of the apparatus, where R is a tissue resistance value of the myocardium of the human patient and C is an effective capacitance value of the capacitor means, and a second time constant that is an average defibrillation chronaxie characteristic time, $d_c$ of the myocardium of the human patient.

8. The apparatus of claim 1 wherein the optimum pulse duration is automatically set by the apparatus to be the sum of;

a first time constant that is a system time constant, RC, of the apparatus, where R is an average tissue resistance of the myocardium of the human patient and C is an effective capacitance of the capacitor means, and a second time constant that is an average defibrillation chronaxie characteristic time, $d_c$, of the myocardium of the human patient, said sum being multiplied by a small factor.

9. The apparatus of claim 8 wherein the small factor is between 0.5 and 0.65.

10. The apparatus of claim 8 wherein the small factor is 0.58.

11. The apparatus of claim 1 wherein the optimal pulse duration is determined by the means for selectively discharging for a first phase of a multiple phase pulse, said first phase being of a consistent polarity.

12. The apparatus of claim 1 wherein the defibrillation waveform includes a first pulse and a second pulse of opposite polarity to the first pulse and wherein the optimal pulse duration is determined by the means for selectively discharging for the first pulse of the defibrillation waveform.

13. The apparatus of claim 12 wherein the optimal pulse duration of the second pulse is determined by the means for selectively discharging to be a second pulse duration value derived from a predetermined total decay percentage of the preselected amount of electrical energy stored in the capacitor less the percentage decay at the start of the second pulse.

14. The apparatus of claim 13 wherein the total decay percentage is between 70% to 90%.

15. The apparatus of claim 14 wherein the total decay percentage is 80%.

16. The apparatus of claim 12 wherein the optimal pulse duration of the second pulse is determined by the means for selectively discharging to be slightly smaller than the optimal pulse duration of the first pulse.

17. The apparatus of claim 12 wherein the optimal pulse duration of the second pulse is determined by the means for selectively discharging to be a second pulse duration value such that a total duration value comprising the sum of the optimal pulse durations of the first and second pulses equals a predetermined absolute time interval.

18. The apparatus of claim 12 wherein the optimal pulse duration of the second pulse is determined by the means for selectively discharging to be a second pulse duration value derived from a predetermined total tilt value for the defibrillation waveform stored by the means for selectively discharging less the tilt percentage of the first pulse.

19. The apparatus of claim 18 wherein the total tilt value is between 70% and 90%.

20. The apparatus of claim 18 wherein the total tilt value is 80%.

21. The apparatus of claim 12 wherein the optimal pulse duration of the second pulse is determined by the means for selectively discharging to be a predetermined absolute time interval.

22. The apparatus of claim 12 wherein the optimal pulse duration of the second pulse is determined by the means for selectively discharging to be a second pulse duration value equal to the time to achieve a predetermined tilt percentage for the second pulse.

23. An improved implantable defibrillator apparatus for producing a capacitive-discharge defibrillation waveform to be delivered through at least two electrodes adapted for implantation in a human patient, the implantable defibrillator apparatus including a self-contained human implantable housing having electrical connections to at least two electrodes adapted for implantation in the human patient, the implantable housing containing a waveform-generating capacitor means for storing an electrical charge, means for charging the waveform-generating capacitor means, and means for selectively discharging the electrical charge in the capacitor means through the at least two electrodes in response to a means for sensing of a cardiac dysrhythmia in the human patient, the improvement comprising:

the means for selectively discharging including means for controlling the discharge of the capacitor means through the at least two electrodes to produce a defibrillation waveform comprising at least one electrical pulse having a predetermined optimum pulse duration based on an optimal system time constant RC, of the apparatus, where R is an average tissue resistance of the myocardium of the human patient and C is an effective capacitance of the capacitor means.

* * * * *